(12) United States Patent
Yokota (10) Patent No.: US 10,010,268 B2
(45) Date of Patent: Jul. 3, 2018

(54) ENDOSCOPE APPARATUS

(75) Inventor: Masayoshi Yokota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 610 days.

(21) Appl. No.: 13/232,699

(22) Filed: Sep. 14, 2011

(65) Prior Publication Data

US 2012/0062724 A1 Mar. 15, 2012

Related U.S. Application Data

(60) Provisional application No. 61/383,009, filed on Sep. 15, 2010.

(51) Int. Cl.
| | | |
|---|---|---|
| *H04N 7/18* | (2006.01) | |
| *A61B 5/107* | (2006.01) | |
| *A61B 1/00* | (2006.01) | |
| *A61B 1/045* | (2006.01) | |
| *A61B 1/06* | (2006.01) | |
| *G01B 11/25* | (2006.01) | |

(52) U.S. Cl.
CPC ........ *A61B 5/1076* (2013.01); *A61B 1/00009* (2013.01); *A61B 1/045* (2013.01); *A61B 1/0638* (2013.01); *A61B 5/1079* (2013.01); *G01B 11/25* (2013.01); *G01B 11/2513* (2013.01)

(58) Field of Classification Search
CPC ..... A61B 5/0084; A61B 1/043; A61B 1/0638; A61B 1/0646; A61B 1/00096; A61B 1/00186; A61B 1/042; A61B 1/05; A61B 5/0071; A61B 17/154; A61B 17/155; A61B 17/157; A61B 17/158; A61B 17/1666

USPC ................ 348/45–50, 65–85; 356/600–626; 600/118, 160, 178–182

See application file for complete search history.

(56) References Cited

U.S. PATENT DOCUMENTS

| | | | |
|---|---|---|---|
| 4,582,809 A * | 4/1986 | Block et al. ................... | 436/527 |
| 5,434,669 A * | 7/1995 | Tabata et al. ................. | 356/477 |
| 5,612,905 A * | 3/1997 | Maillart et al. ............... | 702/153 |
| 6,028,622 A * | 2/2000 | Suzuki ............................ | 348/65 |
| 2003/0078477 A1* | 4/2003 | Kang et al. .................... | 600/178 |
| 2004/0037454 A1* | 2/2004 | Ozawa et al. ................. | 382/128 |
| 2006/0052668 A1* | 3/2006 | Homma ......................... | 600/177 |
| 2006/0132790 A1* | 6/2006 | Gutin ............................. | 356/479 |
| 2007/0208225 A1* | 9/2007 | Czaniera ................ | A61B 1/267 600/178 |
| 2009/0225156 A1* | 9/2009 | Akiyama ........... | A61B 1/00096 348/68 |
| 2009/0225320 A1 | 9/2009 | Bendall et al. | |
| 2009/0225321 A1 | 9/2009 | Bendall et al. | |

(Continued)

*Primary Examiner* — Andy Rao
*Assistant Examiner* — Samuel D Fereja
(74) *Attorney, Agent, or Firm* — Holtz, Holtz & Volek PC (57) ABSTRACT

Provided is an endoscope apparatus for measuring a subject. The endoscope apparatus including: an elongated insertion unit; an image capturing unit being provided on a distal end part of the insertion unit, the image capturing unit configured to obtain an image of the subject; an illumination unit comprising a first light source and configured to illuminate an observation viewing field of the image capturing unit; and a fringe projection unit comprising a second light source configured to emit a light, which differs from a light of the first light source, and a fringe pattern generation unit configured to form the fringe pattern, and configured to project the fringe pattern on the subject.

17 Claims, 6 Drawing Sheets

(56) References Cited

U.S. PATENT DOCUMENTS

| | | | |
|---|---|---|---|
| 2009/0225333 A1 | 9/2009 | Bendall et al. | |
| 2009/0259098 A1* | 10/2009 | Krattiger | A61B 1/00096 600/109 |
| 2009/0306478 A1* | 12/2009 | Mizuyoshi | A61B 1/0638 600/178 |
| 2009/0312607 A1* | 12/2009 | Sunagawa | A61B 1/0638 600/160 |
| 2010/0032546 A1* | 2/2010 | Kawano et al. | 250/205 |
| 2010/0039507 A1* | 2/2010 | Imade | 348/68 |
| 2010/0091292 A1* | 4/2010 | Pfaff | 356/457 |
| 2010/0108873 A1* | 5/2010 | Schwertner | G01B 11/2504 250/252.1 |
| 2010/0158322 A1* | 6/2010 | Weston et al. | 382/113 |
| 2010/0311005 A1* | 12/2010 | Liang | A61B 1/00009 433/29 |
| 2011/0205552 A1* | 8/2011 | Bendall | G01B 11/25 356/606 |
| 2011/0255095 A1* | 10/2011 | Jiang | G01B 9/02004 356/479 |
| 2012/0154576 A1* | 6/2012 | Weston et al. | 348/136 |

* cited by examiner

ENDOSCOPE APPARATUS

The present application claims priority on U.S. Patent Provisional Application No. 61/383,009, filed Sep. 15, 2010, the contents of which are incorporated herein by reference.

BACKGROUND OF THE INVENTION

Field of the Invention

The present invention relates to an endoscope apparatus. To be more specific, the invention relates to an endoscope apparatus which projects a fringe pattern or the like on a subject to thereby measure the three dimensional shape of the surface of the subject.

Description of Related Art

Heretofore, in order to inspect a subject, there is used an endoscope provided with an elongated insertion unit, the distal end of which has an optical system or an observation device such as image capturing device. An endoscope is known that obtains several fringe images, in which a fringe pattern is projected on a subject, while displacing the phase of the fringe pattern, and calculates the three dimensional shape of the subject by a commonly known phase shifting method, using these several fringe images.

For example, U.S. Patent Application, Publication No. 2009/0225333 discloses an endoscope apparatus provided with a light source for illuminating an observation viewing field, and a light source for projecting a fringe pattern. The both light sources are for illuminating white light, and the illumination light sources are controlled to switch off with a shutter when the fringe pattern is projected.

DETAILED DESCRIPTION OF THE INVENTION

Hereunder, a first embodiment of the present invention is described, with reference to FIG. 1 through FIG. 5.

Figure 1:
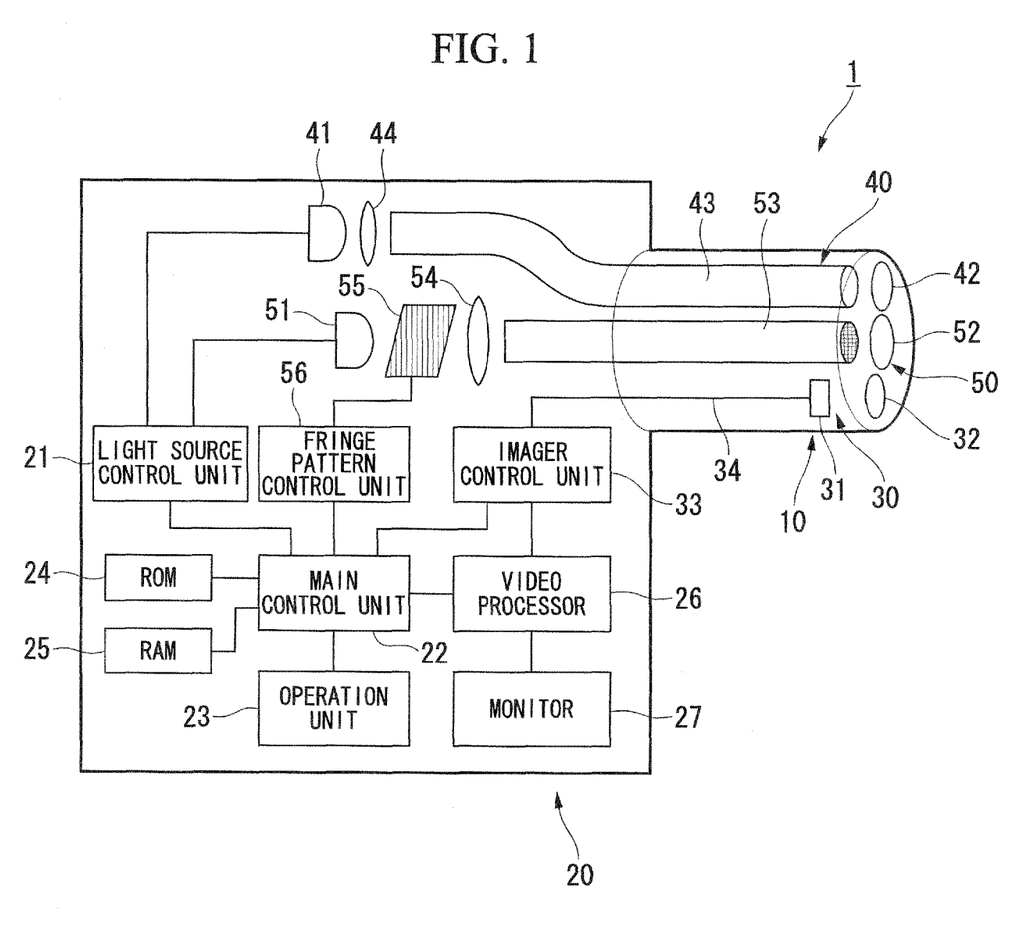
FIG. 1 is a diagram showing an entire configuration of an endoscope apparatus of a first embodiment of the present invention.

FIG. 1 is a diagram showing an entire configuration of an endoscope apparatus 1 of the first embodiment. The endoscope apparatus 1 is used for an internal observation of a subject or an observation of a subject at a difficult access position, and it is provided with an insertion unit 10 and a main body part 20 to which the proximal end of the insertion unit 10 is connected.

The insertion unit 10 is formed in a tube shape, and is inserted into a subject or into an access pathway to a subject. An image capturing unit 30 which obtains images of a subject, an illumination unit 40 which illuminates the observation viewing field in front of the insertion unit 10, and a fringe projection unit 50 which projects a fringe on the subject is provided in the insertion unit 10.

The image capturing unit 30 is provided with an imager 31 arranged in the vicinity of the distal end of the insertion unit 10, an objective optical system 32 arranged in front of the imager 31, and an imager control unit 33 connected to the imager 31.

As the imager 31, an appropriate configuration may be selected from various types of commonly known configurations which include various types of image sensors such as CCDs (Charge Coupled Device) and CMOSs (Complementary Metal Oxide Semiconductor). The objective optical system 32 has a predetermined angle of view, and enters a reflected light within an observation viewing field prescribed by this angle of view irradiate into the imager 31. The imager control unit 33 is provided within the main body part 20, and is connected to the imager 31 via a wiring 34 which extends within the insertion unit 10. The imager control unit 33 controls such as driving and video signal acquisition setting of the imager 31.

The illumination unit 40 is provided with a first light source 41, an illumination optical system 42, a fiber bundle 43 which guides light of the first light source 41 to the illumination optical system 42, and an incident optical system 44 arranged between the first light source 41 and the fiber bundle 43.

The first light source 41 is a commonly-used white light source, and is arranged within the main body part 20. The illumination optical system 42 is attached to the distal end or the vicinity of the distal end of the insertion unit 10, and diffuses and emits an irradiated light from the first light source 41 into a viewing field range appropriate for the angle of view of the objective optical system 32, thereby the irradiated light illuminate the observation viewing field. The fiber bundle 43 extends from the vicinity of the illumination optical system 42 through the insertion unit 10 to the vicinity of the first light source 41 within the main body part 20. There is no particular limitation on the type of the fiber bundle 43, and a commonly-used light guide may be used. The incident optical system 44 converges the emitted light from the first light source 41 to a level similar to the diameter of the fiber bundle 43. Thereby, the incident optical system 44 efficiently guides emitted light into the fiber bundle 43.

The fringe projection unit 50 is provided with a second light source 51, a projection optical system 52, a fiber bundle 53 which guides the light of the second light source 51 to the projection optical system 52, an incident optical system 54 arranged between the second light source 51 and the fiber bundle 53, and a fringe pattern generation unit 55 arranged on an optical path of the light emitted from the second light source 51.

The second light source 51 emits light of a color different from the light emitted from the first light source 41 as fringe pattern projection light. In the present embodiment, the second light source 51 is a red light source, and the second light source 51 emits red light different from the color of light emitted from the first light source 41. The projection optical system 52 is attached to the distal end or the vicinity of the distal end of the insertion unit 10, and diffuses and emits the light irradiated from the second light source 51 into a viewing field range appropriate for the angle of view of the objective optical system 32, thereby the projection optical system 52 suitably projects the fringe within the observation viewing field. The fiber bundle 53 extends from the vicinity of the projection optical system 52 through the insertion unit 10 to the vicinity of the second light source 51 within the main body part 20. As the fiber bundle 53, a so-called image guide in which optical fibers are in an aligned arrangement so that a fringe pattern is suitably projected, is used. The incident optical system 54 converges the light which is emitted from the second light source 51 and has passed through the fringe pattern generation unit 55 to a level similar to that of the diameter of the fiber bundle 53, and an image of the fringe pattern is imaged with the incident optical system 54 on an end surface of the fiber bundle 53. Thereby, the light can be efficiently guided into the fiber bundle 53.

The fringe pattern generation unit 55 is capable of forming a plurality of fringe patterns which shifts phases, and there may be used a commonly known configuration. For instance, a slit plate having a plurality of slits, or a transparent plate composed of a glass or resin or the like to which a plurality of fringe patterns shifting the phase each other is drawn is moved by means of an actuator such as a piezoelectric element.

A liquid crystal shutter module capable of switching between optical permeability and optical impermeability for each element, or a MEMS (Micro Electro Mechanical System) mirror module provided with a micro reflective mirror for each element may be used as the fringe pattern generation unit 55. In this case, by performing control for each element, it is possible to form a plurality of fringe patterns with shifted phases without moving the entire fringe pattern generation unit, and therefore, there is an advantage in that the configuration of the fringe projection unit can be simplified. Fringe pattern switching is performed by a fringe pattern control unit 56 connected to the fringe pattern generation unit 55.

Other mechanisms provided within the main body part 20 are described. The first light source 41 and the second light source 51 are connected to a light source control unit 21 which controls ON/OFF of these light sources. The imager control unit 33, the fringe pattern control unit 56, and the light source control unit 21 are connected to a main control unit 22 which controls the entire endoscope apparatus 1. An operation unit 23, which is arranged in the endoscope apparatus 1 and performs a manipulated input by an operator, is connected to the main control unit 22. Memory media such as a ROM 24 in which a firmware is recorded and a RAM 25 serving as an access memory may be connected to the main control unit 22 as necessary.

Furthermore, a video processor 26 which processes video signals obtained by the imager 31 is connected to the imager control unit 33 and the main control unit 22. A monitor 27 which displays a video signal processed by the video processor 26 as an image is connected to the video processor 26.

Operations of the endoscope apparatus 1 configured as described above in use are described.

First, the operator inserts the insertion unit 10 into a subject or into an access pathway such as pipe line to a subject, and advances the distal end of the insertion unit 10 to a predetermined observation portion. The operator inspects the subject by switching between an observation mode for observing an image of a required portion of the subject and a measuring mode for measuring the three dimensional shape of this portion.

In the observation mode, upon receiving a command from the main control unit 22, the light source control unit 21 controls so that the first light source 41 to turn ON, and controls so that the second light source 51 to turn OFF. As a result, the fringe patterns is not projected from the fringe projection unit 50, and white light is irradiated from the illumination unit 40 onto the observation viewing field while no fringe pattern is projected from the fringe projection unit 50. The observation viewing field is illuminated. The image of the illuminated subject is imaged on the imager 31 through the objective optical system 32. A video signal transmitted from the imager 31 is processed by the video processor 26 and displayed on the monitor 27. The operator can observe the subject with the image of the subject displayed on the monitor 27, and can save the image as necessary.

In the measuring mode, while the ON state of the first light source 41 is maintained, the light source control unit 21 controls so that the second light source 51 to turn ON. Red light emitted from the second light source 51 passes through the fringe pattern generation unit 55 and the incident optical system 54 and is irradiated into the fiber bundle 53. Then, the red light is irradiated on the observation viewing field through the projection optical system 52. Having passed through the fringe pattern generation unit 55, the red light turns into a predetermined fringe pattern, and a red color fringe pattern is projected on the observation viewing field having white light irradiated thereon.

Figure 2:
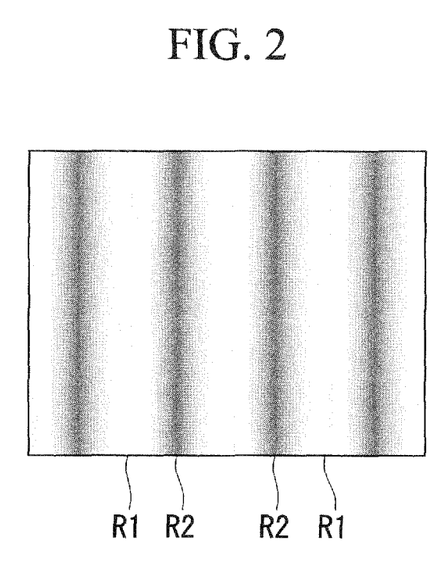
FIG. 2 is an example of a fringe image obtained with the endoscope apparatus.
Figure 3:
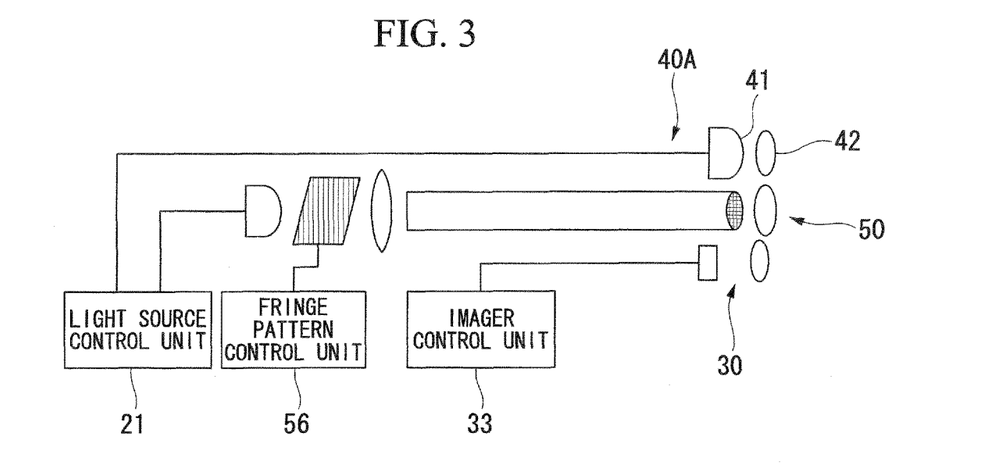
FIGS. 3 to 5 are diagrams schematically showing an image capturing unit, an illumination unit, and a fringe projection unit in a modified example of the endoscope apparatus.

When the operator performs a measurement start input through the operation unit 23, the imager 31 operates by the imager control unit 33, which has received the command from the main control unit 22, and an image of the subject with the fringe pattern projected thereon (first fringe image) is obtained. FIG. 2 shows an example of the first fringe image. In the first fringe image, the surface of the subject illuminated with white light is reflected in regions R1. A red color fringe pattern is reflected in regions R2 and can be identified from white light. The obtained first fringe image is saved on the RAM 25 or on a non-volatile recording medium or the like (not shown in the diagram).

When the first fringe image is acquired, the main control unit 22 operates the fringe pattern generation unit 55 through the fringe pattern control unit 56, to change the fringe pattern to a different fringe pattern that shifts the phase of which is displaced by a predetermined amount from the phase at the time of obtaining the fringe image. Then, the imager 31 obtains and saves an image of the subject with the changed fringe pattern projected thereon. This process is repeated to obtain and save several (normally three or more images) fringe images of the subject having the fringe patterns with mutually displaced phases projected thereon. Then the main control unit 22 uses the obtained images to thereby calculate the three dimensional shape of the subject by means of a commonly known phase shifting method. The calculated information is displayed on the monitor 27 or recorded on the non-volatile recording medium described above.

In a conventional endoscope apparatus which uses a phase shifting method, both of the light source for observation and the light source for fringe patte projection are a white light source in general. Therefore, there is a problem in that if both of the light sources irradiate light at the same time, the projected fringe pattern is erased by the white light for observation, and consequently, images that can be used for the phase shifting method cannot be obtained.

According to the endoscope apparatus 1 of the present embodiment, the first light source 41 of the illumination unit 40 and the second light source 51 of the fringe projection unit 50 respectively emit different light. Therefore, the projected fringe pattern will not be erased even when the observation viewing field is illuminated with the light of the first light source 41. As a result, even in the measuring mode, it is possible to obtain fringe images that can be used in the phase shifting method without controlling the first light source 41 to turn OFF. Accordingly, it is possible to reduce processing time for the measuring mode, and perform a measurement smoothly.

Moreover, when switching from the measuring mode to the observation mode, it is sufficient to control the second light source 51 to turn OFF, and ON control for the first light source 41 is not necessary. As a result, the number of processes regarding to mode switching is reduced, and switching between the measuring mode and the observation mode can be quickly performed.

Furthermore, lights emitted from the first light source 41 and the second light source 51 are respectively introduced to the respective fiber bundles 43 and 53 through the incident optical systems 44 and 54. Therefore, light can be used efficiently.

In the endoscope apparatus 1 of the present embodiment, various modifications may be made to the configuration of the illumination unit and the fringe projection unit. First, in the illumination unit, as with an illumination unit 40A of a modified example shown in FIG. 3, the first light source 41 may be arranged on the distal end side of the insertion unit 10. As the first light source 41 in this case, a small size light source such as a light emitting diode (LED) is preferable. With use of a small light source in this manner, no wide space is required. Moreover, in this case, no fiber bundle 43 needs to be provided through the insertion unit 10.

Figure 4:
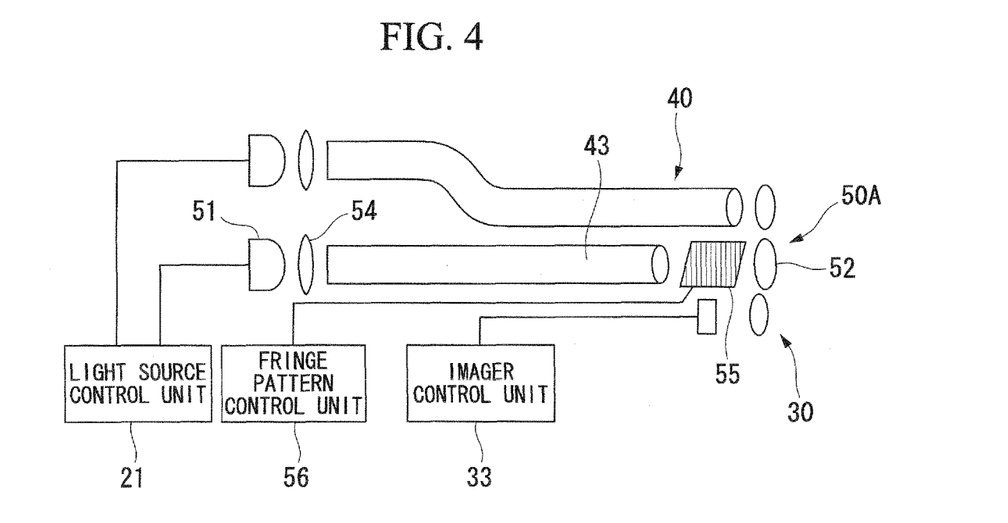
Figure 5:
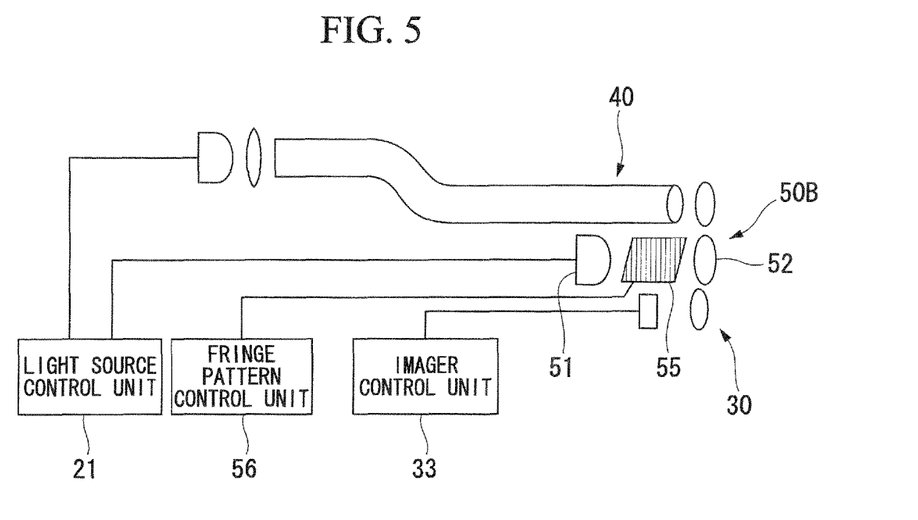

Next, in the fringe projection unit, as with a fringe projection unit 50A of a modified example shown in FIG. 4, the fringe pattern generation unit 55 may be arranged on the distal end side of the insertion unit 10. In this case, the light which has passed through the fringe pattern generation unit 55 is directly irradiated into the observation viewing field from the projection optical system 52. Therefore, the fiber bundle to be arranged between the second light source 51 and the fringe pattern generation unit 55 does not have to be an image guide. Consequently, as with the illumination unit, a commonly-used fiber bundle like a fiber bundle 43 (light guide) can be used as a fiber bundle 53, and manufacturing cost can be reduced. Furthermore, in a case where the fringe pattern generation unit 55 is arranged on the distal end side of the insertion unit 10, as with a fringe projection unit 50B of a modified example shown in FIG. 5, the second light source 51 may be arranged on the distal end side of the insertion unit 10, and be arranged on the proximal end side of the fringe pattern generation unit 55. With this type of configuration, the endoscope apparatus 1 can have a fringe projection unit configured without using a fiber bundle.

The configurations of the illumination unit and the fringe projection unit have been described, using several modified examples. However, when the diameter of the insertion unit 10 needs to be made small, it is preferable that the first and second light sources and the fringe pattern generation unit are arranged within the main body part 20.

Moreover, in the present invention, the aspect of having the light emitted from the first light source 41 and the light emitted from the second light source 51 made different from each other is not limited to the above example of white light and red light. In the present invention, "different light" refers to light being different from the other light in any one of light quantity, light color, and light wavelength.

Accordingly, the illumination light may be white light, and the fringe pattern projecting light may be light with a wavelength different from that of the white light. As the fringe pattern projecting light, for example, there may be used light having a peak outside the visible light range such as infrared rays and ultraviolet rays. In this type of case, a device capable of detecting visible light rays, infrared rays, and ultraviolet rays is used as an imager.

Moreover, the illumination light may be white light and the fringe pattern projecting light may be light of another color other than red. Also, light of a color other than white may be used as light of the illumination unit. Furthermore, while the illumination light and the fringe pattern projecting light are white lights, a halogen lamp may be used as the light source of the illumination unit and a metal halide lamp may be used as the light source of the fringe projection unit, to thereby project a fringe, which can be identified by a difference in light quantity and subtle color shade difference of the white light, on the surface of a subject.

In a case where lights which differ from each other only in light quantity are used as the illumination light and fringe pattern projecting light, the fringe pattern projected by the fringe projection unit is likely to be erased by the illumination light emitted from the first light source. Therefore, the quantity of light to be irradiated from the fringe projection unit 50 onto a subject preferable set to a quantity greater than the quantity of light to be irradiated from the illumination unit 40 onto the subject. At this time, the quantity of light to be irradiated from the fringe projection unit 50 onto the subject is preferably set to a quantity at least twice the quantity of light to be irradiated from the illumination unit 40 onto the subject. This is because the incident light irradiated from the fringe projection unit 50 onto the subject is partly blocked by the fringe pattern generation unit in order to generate a fringe pattern.

Figure 6:
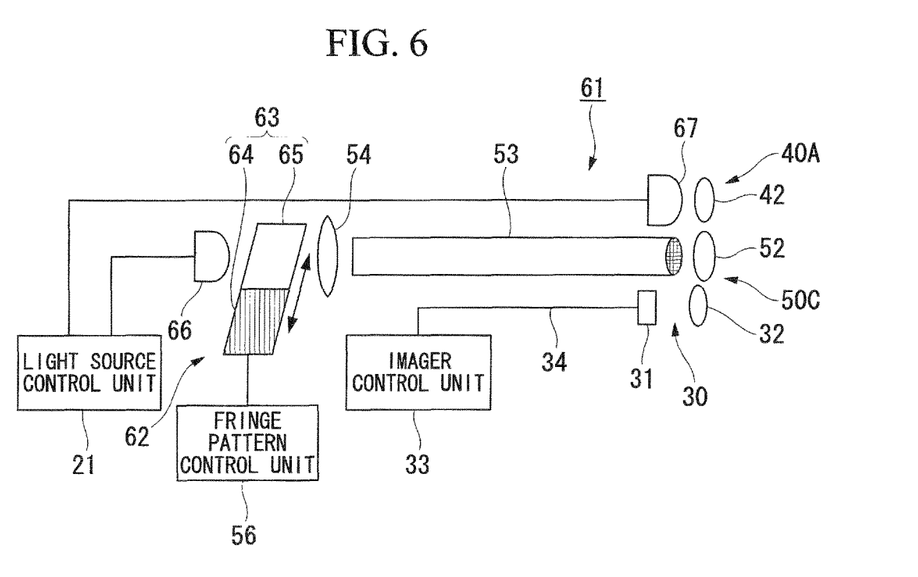
FIG. 6 is a diagram schematically showing an image capturing unit, an illumination unit, and a fringe projection unit in an endoscope apparatus of a second embodiment of the present invention.
Figure 7:
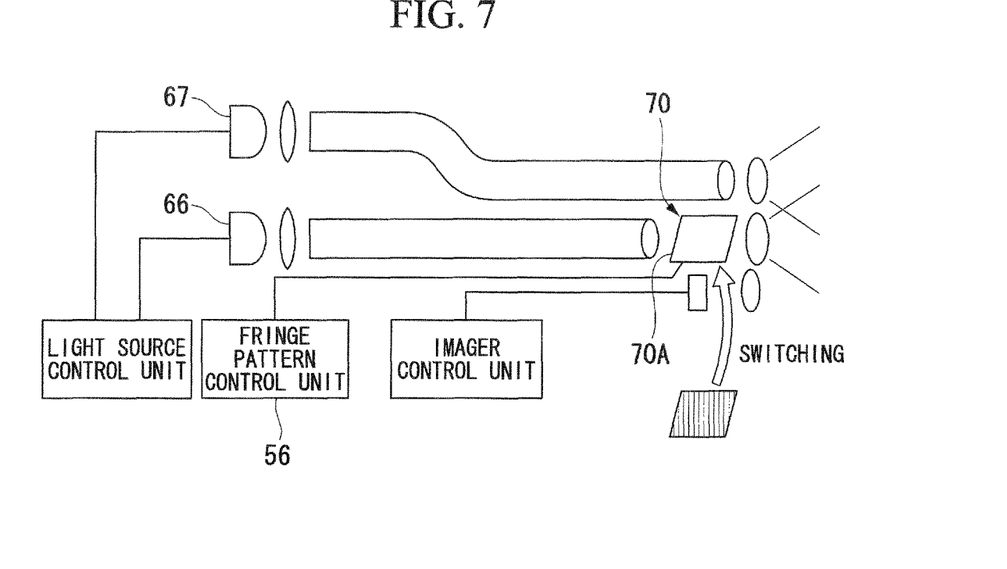
FIGS. 7 and 8 are diagrams schematically showing an image capturing unit, an illumination unit, and a fringe projection unit in a modified example of the endoscope apparatus.
Figure 8:
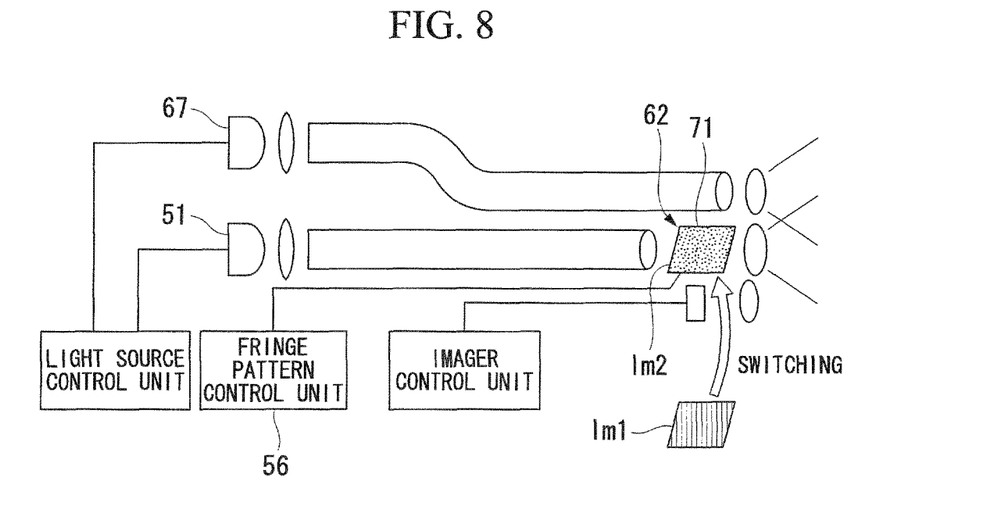

Next, a second embodiment of the present invention is described, with reference to FIG. 6 through FIG. 8. An endoscope apparatus 61 of the present embodiment differs from the endoscope apparatus 1 described above in an aspect of control of the fringe projection unit in the observation mode. In the following description, configurations in common with those described already, are given the same reference signs and overlapping descriptions thereof are omitted.

FIG. 6 is a diagram schematically showing a configuration of an image capturing unit 30, an illumination unit 40A, and a fringe projection unit 50C in the endoscope apparatus 61. A fringe pattern generation unit 62 is provided with a pattern member 63 which has a fringe pattern unit 64 with a plurality of mutually phase-displaced fringe patterns drawn thereon, and which has a transparent unit 65 with no fringe pattern drawn thereon. The fringe pattern generation unit 62 is such that with an actuator (not shown in the diagram), an arbitrary fringe pattern of the fringe pattern unit 64, or the transparent unit 65, can be moved onto an optical pathway between a second light source 66 and an incident optical system 54.

In the endoscope apparatus 61, a first light source 67 of the illumination unit 40 is a white color LED, and the second light source 66 of the fringe projection unit 50C is a metal halide lamp.

Operations of the endoscope apparatus 61 configured as described above in use are described. In the measuring mode of the endoscope apparatus 61, while the ON state of the first light source 67 is maintained, an identifiable fringe pattern is projected on the surface of a subject by the second light source 66 as described above, and a plurality of fringe images are obtained.

On the other hand, in the observation mode, upon receiving a command from a main control unit 22, a fringe pattern control unit 56 controls the actuator, to move the transparent unit 65 of the pattern member 63 onto the optical path between the second light source 66 and the incident optical system 54. Accordingly, the fringe pattern generation unit 62 is switched to a fringe pattern display OFF state where no fringe pattern is projected. The light emitted from the second light source 66 passes through a fiber bundle 53 to be irradiated from the projection optical system 52 as auxiliary illumination light for illuminating the observation viewing field. That is to say, in the observation mode, the lights of the first light source 67 and the second light source 66 are used for illuminating the observation viewing field.

Normally, in a conventional endoscope apparatus which uses a phase shifting method, an illumination unit and a fringe projection unit are separately provided in a narrow space at the distal end side of the insertion unit. Hence there is a problem in that in some cases the quantity of light at the time of performing observation is insufficient with only illumination light from the illumination unit arranged in this small space.

In order to solve this problem, use of a light source with greater light quantity has been considered. However, since the structure is for performing both fringe pattern projection and light illumination from the distal end of the insertion unit, the diameter of the insertion unit needs to be made greater in order to make the illumination light irradiation region at the distal end of the insertion unit greater. Therefore, the method of using a light source with a greater light quantity leads to an increase in cost and has a limited level of effectiveness.

Moreover, in the case where the first light source 67 is arranged within the main body as shown in FIG. 7, it may be considered to make the fiber bundle for guiding illumination light thicker. However, also in this case, the diameter of the insertion unit becomes greater. Furthermore, a method of changing the first light source to a type of light source with a large light quantity may be considered. However, there is a problem in that the size of the device becomes large in order to ensure heat radiation performance to match the light quantity, and this leads to increase in electric power consumption.

For these reasons, it has not been easy to increase the light quantity of illumination light without increasing the diameter of the insertion unit.

According to the endoscope apparatus 61 of the present embodiment, in the observation mode, light of the second light source 66 of the fringe projection unit 50C is irradiated as auxiliary illumination light onto the observation viewing field. As a result, the light quantity of the illumination light at the time of performing observation can be increased, and an observation of a subject can be suitably performed while preventing a shortage in the light quantity of the illumination light.

In the endoscope apparatus of the present embodiment, the fringe pattern generation unit is not limited to one that is provided with the pattern member 63 described above. For example, as shown with the modified example shown in FIG. 7, a liquid crystal shutter module 70 may be provided instead of the pattern member 63. In this case, in the observation mode, the fringe pattern control unit 56 brings all elements of the liquid crystal shutter module 70 into a state 70A in which that light pass through, and the fringe pattern generation unit 62 into a fringe pattern display OFF state. Moreover, the MEMS mirror module described above may be used instead of the liquid crystal shutter module 70.

In addition to this, instead of the pattern member 63, the configuration may be such that a slit plate with a fringe pattern formed thereon is used, and the slit plate is removed from the optical path between the second light source 66 and the incident optical system 54 using an actuator or the like, to thereby bring the fringe pattern generation unit 62 into the fringe pattern display OFF state.

Moreover, the second light source to be used as auxiliary illumination light does not have to be a white light source. For example, in the case where the second light source 51 of the first embodiment, which is a red light source, is used, then as shown with a modified example shown in FIG. 8, a liquid crystal panel 71 provided with a color filter may be used for the fringe pattern generation unit 62.

In this modified example, in the measuring mode, the fringe pattern control unit 56 inputs a fringe image Im 1, which is formed with two light-dark colors such as black and white, on the liquid crystal panel 71, and light is emitted from the second light source 51, to thereby project a fringe pattern. In the observation mode, the fringe pattern control unit 56 inputs a mosaic image Im 2 which uses multiple colors such as blue and green on the liquid crystal panel 71, to bring the fringe pattern generation unit 62 into the fringe pattern display OFF state. That is to say, red light emitted from the second light source 51 is irradiated as backlight onto the liquid crystal panel 71, which is displaying the image Im 2. As a result, the light that has passed through the liquid crystal panel 71 has a color close to white, and it is converted into a state of light emitted from the first light source 67. Therefore, when illuminating the observation viewing field, the light passing through the liquid crystal panel 71 can be made into more appropriate auxiliary illumination light.

In addition, when the second light source emits infrared rays or the like, an infrared ray filter or the like that can be switched ON and OFF may be installed on the optical path, and the filter may be ON-controlled in the observation mode, to use only visible light components which have passed through the filter, as auxiliary illumination light.

Furthermore, when the second light source emits non-white light, the light quantity in the observation viewing field still increases even if the light continues to be irradiated. Therefore, the color conversion described above does not always have to be performed. However, it is preferable to bring the color close to the light of the first light source because it enables more suitable observation.

Moreover, in the observation mode, even if the fringe pattern generation unit is not in the fringe pattern display OFF state and fringe auxiliary illumination light (that is, light similar to that in the measuring mode) is irradiated from the fringe projection unit, a certain level of effect of increase in the light quantity of the illumination light can be achieved. However, it is preferable that the fringe pattern generation unit is in the fringe pattern display OFF state, because the light quantity distribution of the illumination light in the observation viewing field becomes more uniform.

The respective embodiments of the present invention have been described above. However, the present invention is not limited to these embodiments. Addition, omission, replacement, and other modifications may be made to the configuration without departing from the scope of the invention.

For example, in the first embodiment described above, there was described an example in which the light quantity of the first light source is not controlled in the measuring mode. However, there may be performed control of suppressing the light quantity of the first light source so that the level of identifiability of the fringe pattern to be projected becomes higher.

Moreover, in the respective embodiments described above, there is disclosed the technological concept in which the light source of the illumination unit and the light source of the fringe projection unit respectively emit different light in the measuring mode, and the technological concept in which a greater light quantity is obtained with use of the light source of the fringe projection unit in the observation mode. However, these concepts do not always have to be realized at the same time, and may be independently practiced.

Therefore, for example, in an endoscope apparatus which uses only the latter technological concept, in the measuring mode, the first light source may be OFF-controlled so that light is not emitted from the illumination unit.

Figure 9:
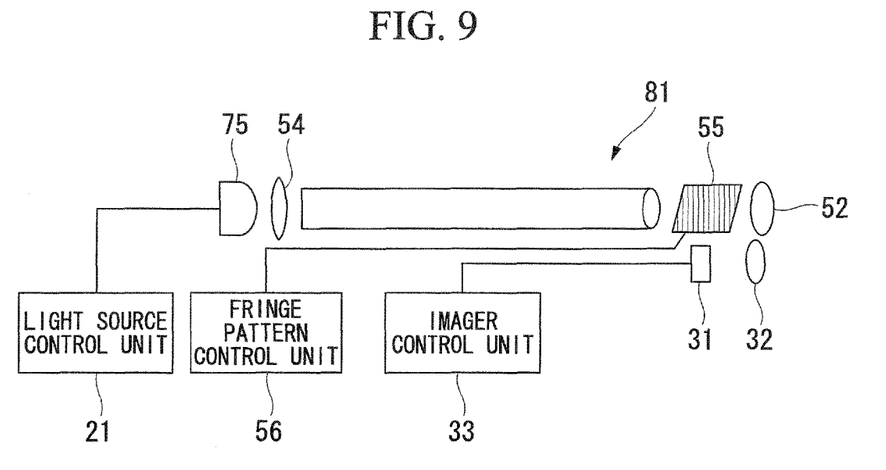
FIG. 9 is a diagram schematically showing an image capturing unit, an illumination unit, and a fringe projection unit in an endoscope apparatus of a modified example of the present invention.

Furthermore, in the respective embodiments described above, there is disclosed the technological concept of providing an incident optical system and a projection optical system in the fringe projection unit, and therefore, this may be independently realized. In this case, as shown with a modified example shown in FIG. 9, an endoscope apparatus 81 may configured such that a single light source 75 functions as a first light source and a second light source. In this case, it is sufficient that only either one of the incident optical system 54 and the projection optical system 52 is provided.

Moreover, the respective embodiments described above take a phase shifting method as an example of a pattern projection method. In addition to this, the endoscope apparatus may be applied with a measuring method which uses another pattern projection such as a light section method and a Fourier transform method. In these cases, the pattern to be projected may be a single pattern as necessary.

Furthermore, the configurations of the respective embodiments and modified examples described above may be appropriately combined without departing from the scope of the invention. Accordingly, the invention is not to be considered as being limited by the foregoing description, and is only limited by the scope of the appended claims.

What is claimed is:

1. An endoscope apparatus for measuring a subject, the endoscope apparatus comprising:
   an insertion portion;
   an imager which obtains an image of the subject;
   an illumination portion including a first light source which emits first light so as to illuminate the subject;
   a fringe projection section including (i) a second light source which emits second light which is different from the first light of the first light source, and (ii) a fringe pattern generator which forms a plurality of fringe patterns by using the second light, so as to project the plurality of fringe patterns on the subject;
   a light source controller which controls the first light source and the second light source, the light source controller (i) controlling the first light source to turn ON and thereby emit the first light and, at the same time, controlling the second light source to turn ON and thereby emit the second light, during an observation mode in which the subject is observed, (ii) controlling the first light source to turn ON and thereby emit the first light and, at the same time, controlling the second light source to turn ON and thereby emit the second light during a measurement mode in which an image of the subject is obtained each time a fringe pattern that is projected on the subject is changed, and (iii) controlling to maintain an ON state of the first light source when switching from the observation mode to the measurement mode;
   a fringe pattern controller which controls the fringe pattern generator (i) to not generate a fringe pattern during the observation mode, and (ii) to form the plurality of fringe patterns during the measurement mode; and
   a controller which controls measurement of the subject by using a plurality of images that have been obtained during the measurement mode.

2. The endoscope apparatus according to claim 1, wherein the fringe pattern controller controls the fringe projection section to project the plurality of fringe patterns on the subject during the measuring mode for obtaining fringe images while the illumination portion illuminates the subject within an observation viewing field of the imager.

3. The endoscope apparatus according to claim 1, wherein the first light has a peak within a visible light range, and the second light has a peak outside the visible light range.

4. The endoscope apparatus according to claim 1, wherein the fringe pattern generator generates the plurality of fringe patterns each of which has a phase, and the phases of the fringe patterns are shifted from each other.

5. The endoscope apparatus according to claim 1, wherein the first light differs from the second light in terms of at least one of light quantity and light wavelength.

6. The endoscope apparatus according to claim 1, wherein the fringe pattern generator comprises a transparent member which does not form a fringe pattern, and
   wherein the fringe pattern controller controls the fringe pattern generator to place the transparent member on an optical path of the second light from the second light source during the observation mode.

7. The endoscope apparatus according to claim 1, wherein the fringe pattern generator comprises:
   a pattern forming member to form the plurality of fringe patterns, and
   wherein the fringe pattern controller controls the fringe pattern generator to place the pattern forming member on an optical path of the second light from the second light source during the measurement mode, and to remove the pattern forming member from the optical path of the second light from the second light source during the observation mode.

8. The endoscope apparatus according to claim 7, wherein the fringe pattern generator further comprises:
   a transparent member which does not form a fringe pattern, and
   wherein the fringe pattern controller controls the fringe pattern generator to place the transparent member on the optical path of the second light from the second light source during the observation mode.

9. The endoscope apparatus according to claim 8, wherein the pattern forming member comprises a fringe pattern member with a plurality of mutually phase-displaced fringe patterns drawn thereon, and
   wherein the transparent member has no fringe pattern drawn thereon.

10. The endoscope apparatus according to claim 7, wherein the pattern forming member comprises a slit plate.

11. The endoscope apparatus according to claim 1, wherein the first light source comprises a white light emitting diode (LED), and
   wherein the second light source comprises a metal halide lamp.

12. The endoscope apparatus according to claim 1, wherein the fringe pattern generator comprises a micro electro mechanical system (MEMS) mirror module.

13. The endoscope apparatus according to claim 1, wherein the fringe pattern generator comprises a liquid crystal shutter module.

14. The endoscope apparatus according to claim 13, wherein, in the observation mode, the fringe pattern controller controls the liquid crystal shutter module to brings all elements of the liquid crystal shutter module into a state in which the second light from the second light source passes through the liquid crystal shutter module.

15. The endoscope apparatus according to claim 1, wherein the fringe pattern generator comprises a liquid crystal panel including a color filter,
   wherein, in the measurement mode, the fringe pattern controller controls the liquid crystal panel to generate a fringe pattern, and
   wherein, in the observation mode, the fringe pattern controller controls the liquid crystal panel to generate a mosaic image including multiple colors.

16. The endoscope apparatus according to claim 15, wherein the second light source comprises a red light source.

17. The endoscope apparatus according to claim 16, wherein the fringe pattern is generated in white and black, and
   wherein the mosaic image includes green and blue.

* * * * *